United States Patent
Buijs et al.

(10) Patent No.: US 6,841,666 B2
(45) Date of Patent: Jan. 11, 2005

(54) PROCESS FOR THE PREPARATION OF ε-CAPROLACTAM

(75) Inventors: Wim Buijs, Schinnen (NL); Henricus Franciscus Wilhelmus Wolters, Echt (NL)

(73) Assignee: DSM IP Assets B.V., Heerlen (NL)

( * ) Notice: Subject to any disclaimer, the term of this patent is extended or adjusted under 35 U.S.C. 154(b) by 13 days.

(21) Appl. No.: 10/473,077

(22) PCT Filed: Mar. 22, 2002

(86) PCT No.: PCT/NL02/00190
§ 371 (c)(1),
(2), (4) Date: Feb. 27, 2004

(87) PCT Pub. No.: WO02/076943
PCT Pub. Date: Oct. 3, 2002

(65) Prior Publication Data
US 2004/0132999 A1 Jul. 8, 2004

(30) Foreign Application Priority Data
Mar. 27, 2001 (EP) .......................... 01201132

(51) Int. Cl.$^7$ ........................................ C07D 201/08
(52) U.S. Cl. .................................................. 540/539
(58) Field of Search ....................................... 540/539

(56) References Cited
U.S. PATENT DOCUMENTS 5,596,070 A * 1/1997 Goetz

FOREIGN PATENT DOCUMENTS

EP 860 431 * 8/1998

* cited by examiner

Primary Examiner—Bruck Kifle
(74) Attorney, Agent, or Firm—Mayer, Brown, Rowe & Maw LLP

(57) ABSTRACT

The invention relates to a process for the preparation ε-caprolactam starting from 6-aminocapronitrile by hydrolysis/oligomerisation followed by de-oligomerisation/cyclisation using superheated steam characterized in that the hydrolysis/oligomerisation is performed with superheated steam converting 6-aminocapronitrile into a molten phase and a gas phase comprising ammonia, ammonia is continuously separated off and the de-oligomerisation/cyclisation is performed by treating the molten phase further with superheated steam. The invention also relates to a process for the preparation of ε-caprolactam starting from 6-aminocapronitrile by hydrolysis/oligomerisation followed by de-oligomerisation/cyclisation characterized in that the preparation is performed in a horizontal scraped-surface reactor, the hydrolysis/oligomerisation is performed with superheated steam converting 6-aminocapronitrile into a molten phase and a gas phase comprising ammonia, ammonia is continuously separated off and the de-oligomerisation/cyclisation is performed by treating the molten phase further with superheated steam.

9 Claims, No Drawings

PROCESS FOR THE PREPARATION OF ε-CAPROLACTAM

CROSS REFERENCE TO RELATED APPLICATION

This application is the National Phase of International Application PCT/NL02/00190 Mar. 22, 2002 which designated the U.S., and that international Application was published under PCT Article 21(2) in English.

The invention relates to a process for the preparation of ε-caprolactam starting from 6-aminocapronitrile by hydrolysis/oligomerisation followed by de-oligomerisation/cyclisation using superheated steam.

Such a process is described in WO-A-9850355. This patent publication describes a process in which 6-aminocapronitrile is converted into ε-caprolactam in the presence of a catalyst. In a first step, a hydrolysis/oligomerisation step, 6-aminocapronitrile is converted into a mixture of oligomers in the liquid phase in water in a closed system in the presence of phosphoric acid as catalyst at a temperature of between 120–250° C. The residence time in the first step is 18 hours. Unconverted 6-aminocapronitrile is subsequently separated from the oligomer mixture using distillation. Omitting this separation step would result in ε-caprolactam yield loss. Thereafter, a de-oligomerisation/cyclisation step is performed wherein the remaining oligomer mixture is treated during more than 7 hours with superheated steam at a temperature of 270–275° C. at atmospheric pressure in the presence of phosphoric acid as catalyst.

A disadvantage of the process according to WO-A-9850355 is that the selectivity to ε-caprolactam after combining several distilled fractions is at most only 87% (based on molar amount of starting 6-aminocapronitrile). Another disadvantage is that the phosphoric acid catalyst will be consumed because ammonium phosphate will be formed due to reaction of phosphoric acid with ammonia. Ammonia is released in the hydrolysis/oligomerisation reaction.

The object of the invention is to provide a more simple process to prepare ε-caprolactam starting from 6-aminocapronitrile with a higher selectivity.

This object is achieved in that the hydrolysis/oligomerisation is performed with superheated steam converting 6-aminocapronitrile into a molten phase and a gas phase comprising ammonia, ammonia is continuously separated off and the de-oligomerisation/cyclisation is performed by treating the molten phase further with superheated steam.

It has been found that with the process of the invention a higher selectivity to ε-caprolactam can be achieved. Another advantage of the process of the invention is that no catalyst needs to be used, as a result of which the end product (ε-caprolactam) contains no catalyst residues and/or the preparation does not comprise a step in which a catalyst must be removed from or deactivated in the ε-caprolactam.

Another advantage is that, in case a non-volatile acidic catalyst (like phosphoric acid) is used in the process of the invention a reduced amount is necessary because less acidic catalyst is consumed due to reaction with ammonia. This is because ammonia is continuously separated off. Another advantage of the process of the invention is that there is no need to separate unconverted 6-aminocapronitrile from the oligomer mixture before subjecting the oligomer mixture to de-oligomerisation/cyclisation, which results in a simpler process. This is advantageous because it is possible to use the reaction mixture obtained from the de-oligomerisation/cyclisation without undue burden for the de-oligomerisation/cyclisation. Separation of mixtures comprising oligomers is as a rule cumbersome because oligomers tend to solidify in pipes and other process equipment which solidification can result in fouling. Another advantage is that in the process of the present invention the conversion of 6-aminocapronitrile into ε-caprolactam can be performed in one reactor. Still another advantage is that in the process of the invention a higher reaction rate can be achieved, especially in the hydrolysis/oligomerisation reaction. Higher reaction rates are advantageous because a smaller volume of process equipment can be used for obtaining comparable degrees of conversion of 6-aminocapronitrile. From an economical/investment point of view smaller process equipment is desired.

WO-A-9837083 describe a process for the preparation of ε-caprolactam starting from 6-aminocapronitrile by a three step process, i.e. (1) contacting 6-aminocapronitrile with water in the liquid phase or in the gas phase respectively, (2) separating water and ammonia, and (3) contacting the resulting liquid mixture with superheated steam at a temperature of between 250 and 400° C. and a pressure of between 0.5 and 2 MPa. In such a process, respectively a liquid or vapor reaction mixture is obtained in step (1) (hydrolysis/oligomerisation) containing oligomers, unconverted 6-aminocapronitrile, water and ammonia. The present invention is different because in the hydrolysis/oligomerisation the reaction mixture is obtained as a melt which mixture mainly contains oligomers and optionally unconverted 6-aminocapronitrile while ammonia is removed with the superheated steam. This is advantageous because the occurrence of degradation reactions is decreased and/or the residence time is reduced. As a rule, degradation reactions result in yield loss and/or in the formation of undesired by-products making the purification more difficult. In the process of the present invention the conversion of 6-aminocapronitrile into ε-caprolactam can be performed in one reactor while in the process of WO-A-9837063 the preparation of ε-caprolactam from 6-aminocapronitrile has to be performed in at least two reactors.

With the term 'hydrolysis' is meant that the nitrile group of 6-aminocapronitrile reacts with water (steam) to an amide group and/or a carboxylic acid group and ammonia, resulting in the formation of 6-aminocaproic acid and/or 6-aminocaproamide.

With the term 'oligomerisation' is meant that 6-aminocapronitrile, 6-aminocaproic acid and/or 6-aminocaproamide oligomerise into oligomers of these monomer components.

With 'converting 6-aminocapronitrile into a molten phase and a gas phase' is meant that 6-aminocapronitrile is hydrolysed and oligomerised with superheated steam resulting in a melt, a molten phase, comprising an oligomer mixture, and a gas phase comprising steam and ammonia.

Most of the oligomer formed in the process of the present invention are oligomers of 6-aminocaproic acid and/or 6-aminocaproamide and oligomers of 6-aminocaproic acid and/or 6-aminocaproamide with 6-aminocapronitrile. Oligomers of 6-aminocaproic acid and/or 6-aminocaproamide can be represented with the following formula $H_2N[(CH_2)_5C(O)NH]_n(CH_2)_5C(O)OH$ or $H_2N[(CH_2)_5C(O)NH]_n(CH_2)_5C(O)NH_2$, in which n is at least 1 (the average n is between 4–7). Oligomers of 6-aminocaproic acid or 6-aminocaproamide with 6-aminocapronitrile can be represented with the following formula $H_2N[(CH_2)_5C(O)NH](CH_2)_5CN$, in which n is at least 1 (the average n is between 4–7).

With the term 'de-oligomerisation' is meant that the oligomers are converted into the corresponding monomer components (i.e. 6-aminocapronitrile, 6-aminocaproic acid and 6-aminocaproamide).

With the term 'cyclisation' meant the cyclisation of 6-aminocaproic acid and/or 6-aminocaproamide into ε-caprolactam.

The reactor to perform the hydrolysis/oligomerisation or the de-oligomerisation/cyclisation preferably is provided with means by which a self-renewing interface between the molten phase and the gas phase is effected with a large surface/volume ratio of the molten phase. For example, the surface/volume ratio of the molten phase is 5 $m^{-1}$, preferably greater than 10 $m^{-1}$, more preferably greater than 40 $m^{-1}$, most preferably greater than 100 $m^{-1}$. The volume ratio molten phase/gas phase is generally less than 2.5. The volume ratio molten phase/gas phase is preferably higher than 1.0, more preferably higher than 1.5.

The process of the invention may be performed in more than one reactor placed in series but preferably is performed in one reactor.

Reactors that have means by which a self/renewing interface between the molten phase and the gas phase is effected are known per se and inter alia comprise stirred gas bubble scrubbers, packed column reactors and horizontal scraped-surface reactors. Horizontal scraped-surface reactors in particular are potentially suitable, since relatively strong mixing of the molten phase can be achieved in these and the molten phase is present in a thin layer, and a large gas volume is present having a relatively high partial pressure of the water vapour. Moreover, it has been found that a thin layer of which the composition is constantly renewed by shear forces, as is the case in scraped-surface reactors is most preferred. Examples of such scraped-surface reactors are described, inter alla, in DE-A-4126425 and BE-A-4649023. Found to be particularly suitable was a reactor of the turbulent-mixer type, in which axial and radial mass transfer is promoted by stirring paddles, which at the same time are provided with scrapers by means of which the product is smeared over the entire internal surface of the horizontal reactor vessel. Such a type of reactor is commercially available, for example from Drais, Mannheim, Del. Therefore the invention also relates to a process for the preparation of ε-caprolactum starting from 6-aminocapronitrile by hydrolysis/oligomerisation followed by de-oligomerisation/cyclisation characterized in that the preparation is performed in a horizontal scraped-surface reactor, the hydrolysis/oligomerisation is performed with superheated steam converting 6-aminocapronitrile into a molten phase and a gas phase comprising ammonia, ammonia is continuously separated off and the de-oligomerisation/cyclisation is performed by treating the molten phase further with superheated steam.

In the process of the invention 6-aminocapronitrile can be fed to the reactor as a mixture. Mixtures comprising 6-aminocapronitrile can be obtained by various processes, for example by hydrogenation of adiponitrile as for example described in U.S. Pat. No. 5723603. A mixture which can for example be used as starting mixture for the present invention comprises between 70 and 100 wt. % 6-aminocapronitrile, between 0 and 15 wt. % of adiponitrile and between 0 and 15 wt. % of hexamethylenediamine, in which the total of these fractions in 100 wt. %. It has been found that the amount of water in the starting mixture is preferably as low as possible.

The 6-aminocapronitrile or mixtures comprising this compound (hereinafter referred to as starting mixture) is preferably fed to the reactor as a liquid.

The hydrolysis/oligomerisation in the process of the invention is preferably carried out by continously passing superheated steam through the 6-aminocapronitrile (or mixtures thereof). During the hydrolysis/oligomerisation 6-aminocapronitrile is converted with superheated steam into a molten phase and a gas phase comprising ammonia, the ammonia is continuously separated off and the molten phase is treated further with superheated steam. If no statement is made to the contrary, all references in the description to steam shall mean superheated steam. The steam has a temperature of between 220 and 450° C. Preferably, the temperature of the steam lies between 220 and 350° C.

In general the 6-aminocapronitrile or a mixture thereof is contacted with the superheated steam at a temperature of between 150 and 300° C. and a pressure of between 0.1 and 2 MPa. Temperatures higher than 300° C. are disadvantageous because of the occurrence of degradation reactors causing yield loss and causing formation of undesired by-products mating the purification more difficult. Temperatures lower than 150° C. are disadvantageous because of the low reaction rate. It has been found that the temperature preferably is between 200 and 270° C. because this results in a further increase of the reaction rate and/or in the oligomer formation. It has also been found that a temperature of between 200 and 250° C. is even more preferred because even more oligomers are formed and/or discoloration of the ε-caprolactum containing reaction mixture is prevented. The pressure is chosen such that, at a given temperature, it is prevented that a aminocapronitrile migrates to the gas phase in a substantial amount. Preferably, the pressure is between 0.2 and 1.2 MPa and the temperature is between 200 and 250° C. More preferably, the pressure is between 0.3 and 0.8 MPa.

At least a part but preferably all of the necessary water for the hydrolysis, is supplied as steam to the starting mixture.

The amount of steam which is present and/or introduced during the hydrolysis/oligomerisation, can vary been wide limits and is higher than or equal to 0.05 kg of $H_2O$ per kg of 6-aminocapronitrile. From an energetic point of view, the amount of steam is preferably as low as possible. The amount of steam is preferably lower than or equal to 1 kg of $H_2O$ per kg of 6-aminocapronitrile and more preferably lower than or equal to 0.3 k of $H_2O$ per kg of 6-aminocapronitrile.

The residence time during the hydrolysis/oligomerisation depends essentially on the amount of 6-aminocapronitrile tolerated in the obtained ε-caprolactam.

The molten phase obtained during the hydrolysis/oligomerisation of the process of the invention mainly comprises oligomers of 6-aminocaproic acid, 6-aminocaproamide and/or 6-aminocapronitrile and optionally unconverted 6-aminocapronitrile.

The gas phase obtained during the hydrolysis/oligomerisation of the process of the invention comprises steam and ammonia. In the process of the invention, the ammonia is continuously separated off. Preferably, the ammonia is continuously separated off with the superheated steam.

The molten phase obtained during the hydrolysis/oligomerisation is by preference directly and without substantial separation of any of the compounds of the mixture, subjected to the de-oligomerisation/cyclisation. This is advantageous because it results in a more simple process.

The de-oligomerisation/cyclisation is performed by contacting the molten phase, obtained by the hydrolysis/oligomerisation, with steam by continuously passing steam through the molten phase at a pressure of between 0.1 and 2 MPa and a temperature of between 250 and 400° C., resulting in a molten phase and a gas phase.

The gas phase obtained during the de-oligomerisation/cyclisation comprising steam, ε-caprolactam and optionally 6-aminocapronitrile, is preferably continuously removed. Temperatures higher than 400° C. are disadvantageous because of the possible occurrence of degradation reactions causing yield loss and causing formation of undesired by-products making the purification more difficult. Temperatures lower than 250° C. are disadvantageous because of the low reaction rate and/or because the produced ε-caprolactam substantially remains in the molten phase. Preferably, the temperature is between 290 and 310° C. because this results in an optimal reaction rate and in an optimal yield to the monomer components. The pressure is chosen such that, at a given temperature, 6-aminocapronitrile and ε-caprolactum migrate to the gas phase in a substantial amount. Preferably, the pressure is between 0.1 and 1.0 MPa.

Preferably, the pressure of the hydrolysis/oligomerisation is the same as the pressure of the de-oligomerisation/cyclisation because this results in a more simple process.

The amount of steam, which is present and/or introduced during the de-oligomerisation/cyclisation, can vary between wide limits and is higher than or equal to 4 kg of $H_2O$ per kg of ε-caprolactam. From an energetic point of view, the amount of steam is preferably as low as possible. The amount of steam is preferably lower than or equal to 10 kg of $H_2O$ per kg of ε-caprolactum.

Although it is advantageous to perform the process of the invention in the substantial absence of a catalyst, the process may be performed in the presence of a homogeneous catalyst. Preferred catalysts are non-volatile acidic catalysts as for example described in WO-A-9850355. Examples are phosphorous containing acidic catalysts such as for example phosphoric acid, diphosphoric acid, metaphosphoric acid, polyphosphoic acid and ortho-phosphorous acid. A preferred example is phosphoric acid. The amount of catalyst can vary between wide limits and is generally between 0.01 and 10 wt. %, preferably 0.1–3 wt. % (relative to the amount of 6-aminocapronitrile).

The process is preferably performed as a continuous process in which the starting mixture is continuously fed to the reactor. The continuously operated process according to the invention can be practiced in a reactor, which is provided with an inlet for the starting mixture, outlets for the steam/ammonia and steam/ε-caprolactum mixtures and means for supplying steam such that the steam is contacted with the starting mixture and the molten phase. The gas phase obtained in the de-oligomerisation/cyclisation will comprise ε-caprolactum, 6-aminocapronitrile and steam. The ε-caprolactum and 6-aminocapronitrile can be isolated from this gaseous mixture by methods known to one skilled in the art. For example, 6-aminocapronitrile is first isolated using distillation and ε-caprolactum is subsequently separated. Preferably, the gaseous mixture is fed to a partial condensation unit and spit in a top stream comprising steam and a liquid bottom stream comprising ε-caprolactam and 6-aminocapronitrile. The partial condensation is preferably performed at a temperature of between 80 and 120° C. The steam can be reused in the process of the invention. The bottom stream is preferably subsequently fed to a distillation column of which the top stream is mainly 6-aminocapronitrile and the bottom stream is mainly ε-caprolactum. The temperature at which the distillation is performed can easily be determined by a man skilled in the art. The 6-aminocapronitrile stream is preferably recycled to the process of the invention. The ε-caprolactum stream can be purified according to conventional techniques, for example extraction, distillation and/or crystallization.

The invention will be elucidated with the following non-limiting examples. The convention in the Examples was calculated as converted molar amount of 6-aminocapronitrile relative to starting molar amount of 6-aminocapronitrile. The selectivity in the Examples was calculated as obtained amount of ε-caprolactam relative to converted molar amount of 6-aminocapronitrile.

EXAMPLE I

A 100 l DRAIS TR 100 test reactor (horizontal tubular reactor equipped with a rotating axis on which mixing and scraping devices are mounted) fitted with a gas inlet and outlet and a pressure controller, was filled with 1.2 kg of 6-aminocapronitrile containing 22.8 g hexamethylene diamine and 28.7 g adipic acid. The reactor was flushed with nitrogen. The reactor was heated to 270° C. at a pressure of 1 MPa. Subsequently, 10 kg/h of superheated steam (temperature of 270° C.) was supplied to the reactor during 4 hours. Subsequently, the reactor (or reaction mixture) was heated to 300° C. and the pressure adjusted to 0.4 MPa. 10 kg/h of superheated steam (temperature of 300° C.) was supplied to the reactor during 3 hours. During 3 hours, steam (containing ε-caprolactum and 6-aminocapronitrile) leaving the reactor was condensed (at 60° C.) and collected. 30 kg of condensed mixture was obtained. Water was evaporated resulting in 1.1 kg of rose-brown liquid. This liquid was analyzed and contained 91 wt. % ε-caprolactam and 9 wt. % 6-aminocapronitrile. The reactor contained approximately 150 grams of residue. The overall conversion was 85 % and the selectivity was 92%.

EXAMPLE II

Example I was repeated with the exception that the reactor was initially heated to 230° C. instead of to 270° C. Also 30 kg of condensed mixture was obtained. Water was evaporated resulting in 1.2 kg of liquid, which was colourless on visual inspection. This liquid was analyzed and contained 82 wt. % ε-caprolactam and 18wt. % 6-aminocapronitrile. The reactor contained less than 50 grams of residue. The overall conversion was 80% and the selectivity was >98%.

What is claimed is:

1. Process for the preparation of ε-caprolactam starting from 6-aminocapronitrile by hydrolysis/oligomerisation followed by de-oligomerisation/cyclisation using superheated steam characterized in that the hydrolysis/oligomerisation is performed with superheated steam converting 6-aminocapronitrile into a molten phase and a gas phase comprising ammonia, ammonia is continuously separated off and the de-oligomerisation/cyclisation is performed by treating the molten phase further with superheated steam.

2. Process according to claim 1 wherein the hydrolysis/oligomerisation is performed in a reactor provided with means by which a self-renewing interface between the molten phase and the gas phase is effected with a large surface/volume ratio of the molten phase.

3. Process according to claim 1, wherein the de-oligomerisation/cyclisation is performed in a reactor provided with means by which a self-renewing interface between the molten phase and the gas phase is effected with a large surface/volume ratio of the molten phase.

4. Process according to claim 1, wherein the surface/volume ratio of the molten phase is greater than 40 m$^{-1}$.

5. Process according to claim 1, wherein the process is performed in one reactor.

6. Process according to claim 1, wherein 6-aminocapronitrile is contacted with superheated steam at a temperature between 150 and 300° C. and a pressure between 0.1 and 2 MPa and the de-oligomerisation/cyclisation is performed at a temperature between 290 and 310° C. and a pressure between 0.1 and 1 MPa.

7. Process according to claim 1, wherein 6-aminocapronitrile is contacted with superheated steam at a temperature between 200 and 250° C.

8. Process according to claim 1, wherein 6-aminocapronitrile is contacted with superheated steam at a pressure between 0.3 and 0.8 MPa.

9. Process for the preparation of ε-caprolactam starting from 6-aminocapronitrile by hydrolysis/oligomerisation followed by de-oligomerisation/cyclisation wherein the preparation is performed in a horizontal scraped-surface reactor, the hydrolysis/oligomerisation is performed with superheated steam converting 6-aminocapronitrile into a molten phase and a gas phase comprising ammonia, ammonia is continuously separated off and the de-oligomerisation/cyclisation is performed by treating the molten phase further with superheated steam.

* * * * *